United States Patent
Ketelson et al.

(10) Patent No.: US 11,395,797 B2
(45) Date of Patent: Jul. 26, 2022

(54) DISSOLVABLE POLYMERIC EYE INSERTS WITH A BIODEGRADABLE POLYMER AND METHOD OF USING SAME

(71) Applicant: Alcon Inc., Fribourg (CH)

(72) Inventors: Howard Allen Ketelson, Dallas, TX (US); Rekha Rangarajan, Fort Worth, TX (US)

(73) Assignee: Alcon Inc., Fribourg (CH)

( * ) Notice: Subject to any disclaimer, the term of this patent is extended or adjusted under 35 U.S.C. 154(b) by 0 days.

(21) Appl. No.: 17/114,931

(22) Filed: Dec. 8, 2020

(65) Prior Publication Data

US 2021/0169781 A1 Jun. 10, 2021

Related U.S. Application Data

(60) Provisional application No. 62/946,060, filed on Dec. 10, 2019.

(51) Int. Cl.
| | |
|---|---|
| A61K 9/00 | (2006.01) |
| A61K 47/10 | (2017.01) |
| A61K 47/32 | (2006.01) |
| A61K 47/34 | (2017.01) |
| A61K 47/36 | (2006.01) |
| A61K 31/357 | (2006.01) |
| A61K 31/498 | (2006.01) |

(52) U.S. Cl.
CPC .......... *A61K 9/0051* (2013.01); *A61K 31/357* (2013.01); *A61K 31/498* (2013.01); *A61K 47/10* (2013.01); *A61K 47/32* (2013.01); *A61K 47/34* (2013.01); *A61K 47/36* (2013.01)

(58) Field of Classification Search
None
See application file for complete search history.

(56) References Cited

U.S. PATENT DOCUMENTS

| | | | |
|---|---|---|---|
| 9,597,328 B2 | 3/2017 | Jain et al. | |
| 2006/0280774 A1 | 12/2006 | Wong et al. | |
| 2009/0155338 A1* | 6/2009 | Conway | A61P 27/02 424/428 |
| 2011/0256185 A1 | 10/2011 | Yang et al. | |
| 2014/0105956 A1 | 4/2014 | Banerjee et al. | |
| 2018/0280313 A1* | 10/2018 | Barman | A61P 27/02 |

FOREIGN PATENT DOCUMENTS

| | | |
|---|---|---|
| CN | 106604695 A | 4/2017 |
| WO | 2016037169 A1 | 3/2016 |

OTHER PUBLICATIONS

Product specification sheet of Vigon, menthone glycerin acetal (MGA); accessed on Dec. 1, 2021. (Year: 2021).*
Karthikeyan, MB et al., Asian J. Pharmaceutics; Oct.-Dec. 2008. 192-200.
Koffler B, et al., Eye Contact Lens; 2010; 36:170-176.
Luchs, J, et al., Cornea, 2010; 29:1417-1427.
McDonald M, et al., Trans Am Ophthalmol. Soc., 2009; 107:214-221.
Paugh et al., Optom Vis Sci. Aug. 2008; 85(8):725-731.
Pescina S et al., Drug Dev Ind Pharm; 2017:1472-1479.
Swanson, Mark, O.D., J. Am. Optom. Assoc., 2011, 69(10):649-655.
Wander A, and Koffler B, Ocul Surf. Jul. 2009;7(3):154-62.

* cited by examiner

*Primary Examiner* — Melissa S Mercier
(74) *Attorney, Agent, or Firm* — Sheng-Hsin Hu

(57) ABSTRACT

Polymeric eye inserts are provided that may be dissolvable when placed in the cul-de-sac of the eye. These inserts may contain one or more mucoadhesive polymers polymers, a biodegradable polymer as well as softener/plasticizer so that, when inserted into the eye, they may absorb tears, and dissolve and slowly release lubricant into the tear film to lubricate and protect the ocular surface for an extended duration of time. The biodegradable polymer containing eye insert may increase dissolution time on the ocular surface for longer lasting relief, may reduce dosing frequency and patient burden typically associated with topical drop usage. These polymeric eye inserts also may include one or more pharmaceutically active agents.

19 Claims, No Drawings

DISSOLVABLE POLYMERIC EYE INSERTS WITH A BIODEGRADABLE POLYMER AND METHOD OF USING SAME

FIELD OF THE DISCLOSURE

The present disclosure generally relates to polymeric eye insert technology, and more particularly to dissolvable polymeric eye inserts having a biodegradable polymer and the eye inserts release lubricants and drugs into the eye (including, but not limited to the anterior and posterior segments) for an extended duration of time compared to topical drop dosage forms.

BACKGROUND

Many ophthalmic formulations comprise compounds that provide lubricity and other desirable properties. When these formulations are instilled in the eye, the properties of such compounds can prevent undesirable problems such as bioadhesion and the formation of friction-induced tissue damage, as well as encourage the natural healing and restoration of previously damaged tissues.

Compliance with administration of topically applied ophthalmic formulations such as liquids, ointments, gels, sprays is often poor, specifically for the treatment of dry eye, allergy, infection and slowly progressing diseases, such as glaucoma, requiring multiple applications per day to lubricate and deliver a drug to the eye. Exposure to topically administered aqueous formulations is often driven by the short retention time of the formulation on the ocular surface, which can be less than 25 minutes following instillation. Paugh et al., Optom Vis Sci. 2008 August; 85(8):725-31. Typical aqueous formulations for ocular use may be diluted or washed from the ocular surface within minutes, introduce variability in the usage, or result in less accurate and precise dosages administered to the eye. Accordingly, there is a need to reduce treatment burden and improve compliance.

Ointments and gels, which are highly viscous and usually reside in the eye longer than a liquid can provide for more accurate administration. However, they can also interfere with a patient's vision and may require, at a minimum, dosing 2-3 times per day. For these and other reasons the rate of discontinuation of use can be very high. Swanson, M., J. Am. Optom. Assoc., 2011; 10:649-6.

Inserts, both bioerodible and non-bioerodible, are also available and allow for less frequent administration. Pescina S et al., Drug Dev Ind Pharm; 2017 May 7:1-8; Karthikeyan, M B et al., Asian J. Pharmacol; 2008; October-December 192-200. These inserts, however, require complex and detailed preparation and can be uncomfortable to the patient. An additional problem with non-bioerodible inserts is that they must be removed after use. However, with proper use and adequate patient education, inserts can be an effective and safe treatment choice for dry eye patients.

Hydroxypropyl cellulose ophthalmic inserts such as LACRISERT® (Aton Pharmaceuticals Inc.) have been used for dry eye patients. These inserts are translucent cellulose-based rods measuring 1.27 mm in diameter and 3.5 mm in length. Each of these inserts contains 5 mg of hydroxypropyl cellulose, with no preservatives or other ingredients. The medication is administered by placing a single insert into the inferior cul-de-sac of the eye beneath the base of the tarsus. These inserts are indicated particularly for patients who continue to have dry eye symptoms following an adequate trial therapy with artificial tears. They also are indicated for patients with keratoconjunctivitis sicca, exposure keratitis, decreased corneal sensitivity, and recurrent corneal erosions. Several studies have been performed to evaluate the efficacy of HPC ophthalmic inserts. (Luchs, J, et al., Cornea, 2010; 29:1417-1427; Koffler B, et al., Eye Contact Lens; 2010; 36:170-176; McDonald M, et al., Trans Am Ophthalmol. Soc., 2009; 107:214-221; Wander A, and Koffler B, Ocul Surf. 2009 July; 7(3):154-62).

However, there also are challenges in using these types of inserts. For example, LACRISERT® inserts tend to dissolve slowly and can remain in the eye even after 15-20 hours. The rod is hard and inelastic with edges due to rod-shaped design. The slow dissolving properties coupled with the rod hardness and design may lead to side effects including blurred vision, foreign body sensation and/or discomfort, ocular irritation or hyperemia, hypersensitivity, photophobia, eyelid edema, and caking or drying of viscous material on eyelashes. The most common side effect of these hydroxypropyl cellulose ophthalmic inserts is blurred vision due to the long retention time of the insert.

There are additional approaches to develop polymeric eye inserts that are comfortable, have a longer dissolution time to release lubricants and drugs and improve patient compliance.

SUMMARY

The invention provides a polymeric eye insert, the insert comprising:
a biodegradable polymer and one or more mucoadhesive polymers that are biocompatible with the ocular surface and tear film of the eye; and
wherein the biodegradable polymer increases a dissolution time of the polymeric eye insert by at least 15 percent comparing to the control polymeric eye insert which is the same polymeric eye insert except the biodegradable polymer is not present.

The invention also provides a method for treating an ocular disorder, which comprises applying the polymeric eye insert according to embodiments of the present disclosure to the cul-de-sac of the eye.

The present invention is partly based on the finding that adding a biodegradable polymer to a polymeric eye insert of mucoadhesive polymers that are biocompatible with the ocular surface and tear film of the eye increases dissolution time of the polymeric eye insert. The biodegradable polymer containing eye insert increases dissolution time on the ocular surface for longer lasting relief, may reduce dosing frequency and patient burden typically associated with topical drop usage. These polymeric eye inserts also may include one or more pharmaceutically active agents.

The insert also has a thickness and elasticity that is relatively comfortable for the user. A preferred thickness is between 50-250 microns, and a most preferred thickness is between 70-150 microns. The target thickness is 90 microns for films dissolving in less than 2 hours

DETAILED DESCRIPTION

Unless defined otherwise, all technical and scientific terms used herein have the same meaning as commonly understood by one of ordinary skill in the art to which this invention belongs. Generally, the nomenclature used herein and the laboratory procedures are well known and commonly employed in the art. Conventional methods are used for these procedures, such as those provided in the art and various general references. Where a term is provided in the singular, the inventors also contemplate the plural of that term. The nomenclature used herein and the laboratory procedures described below are those well-known and commonly employed in the art.

"About" as used herein means that a number referred to as "about" comprises the recited number plus or minus 1-10% of that recited number.

As used in this application, "dissolution time" refers to the time taken for the insert to completely dissolve i.e. break down from a solid gel like material in a vehicle under specified condition to form a homogeneous solution. The dissolution time is measured by the procedure described here: 6 mm diameter film disks were cut and placed in a separate 4 ml vials. DI water (2 ml) was added to each vial and capped. Each vial was vigorously shaken by hand until the insert had dissolved by visual inspection. The dissolution time was recorded. Here, vigorously is defined as the vial was shaken by hand with about 90 times per minute and each shaken is about 3.5 feet in length up and down. Shaken with up and down is counter as two times.

The phrase "percent increase of dissolution time" in the biodegradable polymer increases a dissolution time of the polymeric eye insert by at least 15 percent comparing to the control polymeric eye insert which is the same polymeric eye insert except the biodegradable polymer is not present refers to the following formula:

Percent of increase of dissolution time=
$\{[T_{biodegradable\ polymer} - T_{control}]/T_{control}\} \times 100\%$ wherein: $T_{biodegradable\ polymer}$ is the dissolution time of the insert containing the biodegradable polymer.

$T_{control}$ is the dissolution time of the control insert which is the same polymeric eye insert except the biodegradable polymer is not present.

Embodiments of the present disclosure provide a polymeric eye insert comprising an ocular lubricant. In an embodiment of the present disclosure, a polymeric eye insert may be comprised of a biodegradable polymer, hyaluronic acid, hydroxypropyl guar (HP guar), and a plasticizer, such as polyethylene glycol (PEG). However, other polymers and plasticizers/softeners may be used without departing from the present disclosure, as described herein. An insert according to embodiments of the present disclosure may be inserted in the lower eye lid (also known as the cul-de-sac) of the eye, and upon insertion, the insert may rapidly absorb tears and dissolve to release the ocular lubricant into the tear film to lubricate and protect the ocular surface for an extended duration superior to previously known topical ophthalmic compositions. Pharmaceutically active agents also may be incorporated into polymeric eye inserts according to embodiments of the present disclosure. Insertion of a polymeric eye insert according to embodiments of the present disclosure may provide relief to the patient from symptoms of dry eye as well as other eye conditions.

The biomaterial for forming a polymeric eye insert according to embodiments of the present disclosure may be comprised of one or more polymers that are biocompatible with the ocular surface and tear film. Polymers that may be used in polymeric eye inserts according to embodiments of the present disclosure include, but are not limited to, hyaluronic acid (in acid or salt form), hydroxypropylmethylcellulose (HPMC), methylcellulose, tamarind seed polysaccharide (TSP), Galactomannans, for examples; guar and derivatives thereof such as hydroxypropyl guar (HP guar), scleroglucan poloxamer, poly(galacturonic) acid, sodium alginate, pectin, xanthan gum, xyloglucan gum, chitosan, sodium carboxymethylcellulose, polyvinyl alcohol, polyvinyl pyrrolidine, carbomer, polyacrylic acid and/or combinations thereof.

The preferred biocompatible polymers are hyaluronic acid, guar and derivatives and/or combinations thereof. Hyaluronic acid is an unsulphated glycosaminoglycan composed of repeating disaccharide units of N-acetylglucosamine (GlcNAc) and glucuronic acid (GlcUA) linked together by alternating beta-1,4 and beta-1,3 glycosidic bonds. Hyaluronic acid is also known as hyaluronan, hyaluronate, or HA. As used herein, the term hyaluronic acid also includes salt forms of hyaluronic acid such as sodium hyaluronate. A preferred hyaluronic acid is sodium hyaluronate. The weight average molecular weight of the hyaluronic acid used in insert of the present invention may vary, but is typically weight average molecular weight of 0.1 to 2.0 M Daltons. In one embodiment, the hyaluronic acid has a weight average molecular weight of 0.5 to 1 MDaltons. In another embodiment, the hyaluronic acid has a weight average molecular weight of 1.5 to 2.0 M Daltons.

The galactomannans of the present invention may be obtained from numerous sources. Such sources include from fenugreek gum, guar gum, locust bean gum and tara gum. Additionally, the galactomannans may also be obtained by classical synthetic routes or may be obtained by chemical modification of naturally occurring galactomannans. As used herein, the term "galactomannan" refers to polysaccharides derived from the above natural gums or similar natural or synthetic gums containing mannose or galactose moieties, or both groups, as the main structural components. Preferred galactomannans of the present invention are made up of linear chains of (1-4)-.beta.-D-mannopyranosyl units with .alpha.-D-galactopyranosyl units attached by (1-6) linkages. With the preferred galactomannans, the ratio of D-galactose to D-mannose varies, but generally will be from about 1:2 to 1:4. Galactomannans having a D-galactose:D-mannose ratio of about 1:2 are most preferred. Additionally, other chemically modified variations of the polysaccharides are also included in the "galactomannan" definition. For example, hydroxyethyl, hydroxypropyl and carboxymethylhydroxypropyl substitutions may be made to the galactomannans of the present invention. Non-ionic variations to the galactomannans, such as those containing alkoxy and alkyl (C1-C6) groups are particularly preferred when a soft gel is desired (e.g., hydroxylpropyl substitutions). Substitutions in the non-cis hydroxyl positions are most preferred. An example of non-ionic substitution of a galactomannan of the present invention is hydroxypropyl guar, with a molar substitution of about 0.4. Anionic substitutions may also be made to the galactomannans. Anionic substitution is particularly preferred when strongly responsive gels are desired, Preferred galactomannans of the present invention are guar and hydroxypropyl guar. Hydroxypropyl guar is particularly preferred. The weight average molecular weight of the Hydroxypropyl guar in the insert of the present invention may vary, but is typically 1 to 5 M Daltons. In one embodiment, the Hydroxypropyl guar has a weight average molecular weight of 2 to 4 MDaltons. In another embodiment, the Hydroxypropyl guar has a weight average molecular weight of 3 to 4 M Daltons.

Polymers used in inserts according to embodiments of the present disclosure should be non-toxic and able to solubilize in eye fluids to ensure that the insert is eventually dissolved, generally over a 60-minute time frame. It should be appreciated that the polymer(s) selected should be mucoadhesive. It also should be appreciated that one or more polymers may be blended according to embodiments of the present disclosure. For example, in an embodiment of the present disclosure, hyaluronic acid (HA) may be blended with tamarind seed polysaccharide (TSP) because TSP has been shown to increase residence time of HA in aggregate blends and the blend has desired film mechanical and lubrication properties.

In other embodiments of the present disclosure, as described in further detail below, hyaluronic acid may be combined with HP guar.

In another embodiment of the present disclosure, the polymeric eye insert further comprises a biodegradable polymer, wherein the biodegradable polymer increases a dissolution time of the polymeric eye insert by at least 15 percent comparing to the control polymeric eye insert which is the same polymeric eye insert except the biodegradable polymer is not present.

The biodegradable polymer present in the polymeric insert in an amount sufficient to increase a dissolution time of the polymeric eye insert by at least about 15%, preferably by at least about 25%, more preferably by at least about 35%, in comparison to the control polymeric eye insert which is the same polymeric eye insert except the biodegradable polymer is not present.

Any kind of biodegradable polymer can be used in this application, for example, polyglycolic acid (PGA), Polyhydroxy butyrate (PHB), Polyhydroxy butyrates-co-beta hydroxyl valerate (PHBV), Polycaprolactone (pcl), Nylon-2-nylon-6, polylactic acid (PLA), poly(lactic-co-glycolic) acid (PLGA), and poly(caprolactone). A preferred biodegradable polymer for this patent application is polylactic acid (PLA), poly(lactic-co-glycolic) acid (PLGA), or poly(caprolactone). A more preferred biodegradable polymer is polylactic acid, poly(lactic-co-glycolic). An even more preferred biodegradable polymer is poly(lactic-co-glycolic) (PLGA). Biodegradable polymers are a special class of polymer that breaks down after its intended purpose by bacterial decomposition process to result in natural byproducts such as gases ($CO_2$, $N_2$), water, biomass, and inorganic salts. These polymers are found both naturally and synthetically made, and largely consist of ester, amide, and ether functional groups. Their properties and breakdown mechanism are determined by their exact structure. These polymers are often synthesized by condensation reactions, ring opening polymerization, and metal catalysts. There are vast examples and applications of biodegradable polymers. Bio-based packaging materials have been introduced as a green alternative in the past decades, among which, edible films have gained more attention due to their environmentally-friendly characteristics, vast variety and availability, non-toxicity, and low cost.

One of the most commonly used biodegradable polymers for packaging purposes is polylactic acid (PLA). The production of PLA has several advantages, the most important of which is the ability to tailor the physical properties of the polymer through processing methods. PLA is used for a variety of films, wrappings, and containers (including bottles and cups). In 2002, FDA ruled that PLA was safe to use in all food packaging.

The prefer biodegradable polymer for this patent application is a lactic acid copolymer; As used herein, "a lactic acid copolymer" generally means a copolymer (PLGA) comprising lactic acid units and glycolic acid units. However, malic acid, glyceric acid, or tartaric acid, etc. can also be used instead of glycolic acid. "A lactic acid copolymer" also includes a copolymer consisting of lactic acid units in a molar ratio of 100%, i.e., poly (lactic acid). A lactic acid unit may be in a L-, D-, or DL-form.

When the eye insert is prepared, the addition of PLGA (commercially available from Polysciences, Inc.) to the insert will consider the ratio of lactic acid units and glycolic acid units and the molecular weight o (commercially available from f the copolymer. The molar content of the lactic acid units in the copolymer for the eye insert of the present patent application is preferably 50 to 100%. The molar content of the glycolic acid units is preferably 0 to 50%. The molecular weight of the copolymer affects the tensile strength of the eye insert. Comparing at the same adding amount of PLGA biodegradable polymer to the eye insert, as the molecular weight becomes higher, the tensile strength of the eye insert is increased. For the present patent application, the molecular weight of the copolymer is preferably 10,000 or more but preferably 1,000,000 or less. Thus, the weight-average molecular weight of the PLGA copolymer is preferably from 10,000 to 1,000,000. Comparing to the same adding amount of PLGA to the eye insert, taking into consideration the dissolution time of the eye insert, the ratio of lactic acid units and glycolic acid units is in the range from 100/0 to 50/50.

In some embodiments, the biodegradable polymer is present in amount of from about 0.5%% to about 10%, about 1% to about 5%; the one or more mucoadhesive polymers are present in an amount of from about 50% to about 95% w/w, about 60% to about 90% w/w, about 70% to about 85% w/w, or about 80% to about 90% w/w by dry weight of the polymeric eye insert, provided that the sum of the % w/w of mucoadhesive polymers and % w/w of the biodegradable polymer and other components not listed above is 100% w/w.

The overall dry weight or mass of the polymeric eye insert may be in the range of about 1 to about 10 mg, or about 2 to about 8 mg, and in particular embodiments may be from about 2.5 to about 5 mg.

In some embodiments of the present disclosure, a softener and/or plasticizer may be added to the one or more polymers to facilitate fabrication of a softer, malleable delivery system and also provide improved comfort upon insertion. A plasticizer may soften the material to provide for desirable dissolution rates. It should be appreciated that softeners and/or plasticizers may be low or high-molecular weight compounds, including not limited to, polyethylene glycol (PEG) and derivatives thereof, water, Vitamin E, and triethyl citrate.

In some embodiments, the plasticizer or softener is present in an amount of from about 2% to about 25% w/w, about 5% to about 20% w/w, about 5% to about 15% w/w, or about 5% to about 10% w/w by dry weight of the polymeric eye insert, provided that the sum of the % w/w of mucoadhesive polymers and % w/w of the biodegradable polymer and other components not listed above is 100% w/w.

In some embodiments, the polymeric eye insert may have a water content of about 1% to about 50% after hydration. In particular embodiments, the polymeric eye insert may have a water content of 30-40%.

The polymeric eye insert may be of any size or shape suitable for administration to the eye. Exemplary shapes include film, a rod, a sphere, or an irregular shape having a maximum size in any single dimension of 5-6 mm.

In some embodiments, the polymeric eye insert has a thickness of about 50-400 μm, about 100-300 μm, about 150-250 μm, or about 200 μm.

In particular embodiments, the polymeric eye insert has a thickness of about 150-250 μm, and a water content of 30 to 50% w/w.

In some embodiments of the present disclosure, the polymeric eye insert does not include an additional pharmaceutically active agent. In other embodiments, the polymeric eye insert may include one or more additional pharmaceutically active agents. In some embodiments, the one or more pharmaceutically active agents may be selected from the group of ocular lubricants, anti-redness relievers such as alpha-2 adrenergic agonists such as brimonidine, apraclonidine etc, sympathomimetic amines such as tetrahydrozoline, naphazoline, TRPM8 agonists such as menthol, menthol analogs, steroids and nonsteroidal anti-inflammatory agents to relieve ocular pain and inflammation, antibiotics, antihistamines such as olopatadine, anti-virals, antibiotics and anti-bacterials for infectious conjunctivitis, anti-muscarinics such as atropine and derivatives thereof for myopia treatment, and glaucoma drug delivery such as prostaglandin and prostaglandin analogs such as travoprost, or therapeutically suitable combinations thereof.

Polymeric eye inserts according to embodiments of the present disclosure may be made using various processing techniques, including but not limited to, compression molding and solution casting. Compression molding may be carried out at temperatures and pressures that do not change the material or lead to significant side reactions. For example, compression molding of partially hydrated polysaccharides may use a compressional force of approximately 5,000-12,000 pounds at approximately 200-300 degrees Celsius for approximately 1-2 minutes. Solution or film casting may be carried out using solvents and/or co-solvents that may provide homogeneous films with little to no defects. The solvent may be removed by air or vacuum drying, resulting in an insert material that may be free from residual solvents. For example, a 1% (w/v) aqueous solution of polymer (or blend) may be cast and then allowed to evaporate. The film may then be cut with an oval-shaped punch of desired size and geometry. While compression molding and solution/film casting have been described, it should be appreciated that other processing techniques may be used without departing from the present disclosure.

In one embodiment, the film casting method used was found to generate reproducible inserts and good structural integrity. In this embodiment, distilled water was placed in a 1 L Erlenmeyer flask followed by the addition of the polymer (s). The flask was placed in a sonicator and attached to an overhead mechanical stirrer. The mixture was sonicated and stirred for 60 minutes at 30° C. The speed of the mechanical stirrer was adjusted to 700 rpm and allowed to stir for 60 minutes. The stirring was stopped and the plasticizer (PEG and/or PVP) was added to the flask. This mixture was stirred for 30 minutes under sonication at 700 rpm at 30° C. until a homogeneous, clear solution was obtained. The mechanical stirring was then stopped and the sonication was allowed to continue for an additional 30 minutes in order to remove all bubbles. The Erlenmeyer flask was then removed from the sonicator and left to sit at room temperature for 30 minutes. For the preparation of the films, a petri dish (150 mm diameter×15 mm height) was filled with about 150 g±2 g of the stock solution. The stock solution was subjected to different evaporation techniques evaluation. In a first experiment, a vacuum oven at 50° C. was used. The petri dishes were placed in the oven and the oven was evacuated using a vacuum pump. After 30 hours, the films obtained were yellow in color and some of the films exhibited curved surfaces. The experiments were repeated at 45° C., 40° C., and 35° C., under the same vacuum conditions. All of the experimental conditions above yielded colored films or films with non-uniform weight distribution. It was also observed that the higher the temperature, the darker and more intense the yellow color became. A preferred evaporation technique included evaporation in a chamber equipped with a variable-speed exhaust at room temperature. The airflow, temperature, and humidity were all measured during the evaporation process. The technique described above produced uniform evaporation and films with consistent thickness.

As previously discussed, in vivo studies indicate that traditional topical ophthalmic lubricants do not remain in the eye longer than approximately 25 minutes. However, use of one or more polymers combined with a plasticizer/softener, such as HP guar and hyaluronic acid blended with a plasticizer (such as PEG), may provide flexible films with tunable hydration and dissolution rates for comfortable insertion. While certain embodiments of the present invention are polymeric eye inserts containing a blend of hyaluronic acid, HP guar and PEG, it should be appreciated that other blends may be employed for polymeric eye inserts according to other embodiments of the present disclosure.

The eye inserts of the present disclosure are a platform to deliver lubricants and other pharmaceutically active agents to treat ocular surface symptoms (such as redness, itching and dryness). In some embodiments, the polymeric eye inserts can be used to prolong exposure of pharmaceutically active agents or provide extended drug delivery of pharmaceutically active agents to the eye. Thus, in some embodiments, the present disclosure provides a method of providing extended drug delivery or prolonging exposure of a pharmaceutically active agent to the eye, by administering a polymeric eye insert including the pharmaceutically active agent to a patient in need thereof.

In some embodiments, the present disclosure provides a method of treating or reducing the signs and/or symptoms of dry eye disease (keratoconjunctivitis sicca), comprising administering a polymeric eye insert according to the present disclosure to a patient in need thereof.

The following non-limiting Examples are provided to illustrate embodiments of the invention.

EXAMPLES

Example 1—Polymeric Eye Insert Containing Alpha-2-Adrenergic Agonist

In another invention, insert film was prepared with an alpha-2 adrenergic receptor agonist such as brimonidine at different concentrations i.e. 90 ppm, 495 ppm and 5048 ppm respectively.

Preparation of Control Insert Films_Brimonidine:

300 ml of DI water was transferred from a graduated cylinder to a clean 500 mL Erlenmeyer flask. HA (0.94 g) and PVP (0.21 g) were added into 500 ml Erlenmeyer flask. After stirring the mixture for 1.5 hrs, a homogenous solution was obtained. HP Guar (0.84 g) was added and the mixture was stirred for one hour, the mixture was once again homogenous. PEG (0.21 g) was added and the mixture was stirred for an additional 30 min. The mixture was then allowed to rest (no stirring) for 30 min to remove air bubbles. The mixture (150 g) was poured into a petri dish that was then placed in an evaporation oven (27±3° C.) for two days to produce a film.

Insert Film Hydration Procedure: The film was cut into 6 mm disks with a disk cutter. Note: Each disk was measured for thickness before hydration. Two disks were placed into the middle of a pouch which contained 3 μl of DI water at one bottom corner of the pouch. The pouch was sealed with a heat sealer.

Preparation of Films Containing 100 ppm Brimonidine Tartrate

Initial stages as per the Procedure in the preparation of control insert film_brimonidine. Following the addition of PEG and 30 min of stirring, 2 ml of a 0.52 mg/ml brimonidine tartrate solution in DI water was added and the mixture was stirred for 15 min. All remaining steps were carried out as detailed under film preparation/hydration section above.

Preparation of Films Containing 500 ppm Brimonidine Tartrate

Initial stages as per the Procedure in the preparation of control insert film_brimonidine. Following the addition of PEG and 30 min of stirring, 0.4 ml of a 0.52 mg/ml brimonidine tartrate solution in DI water was added and the mixture was stirred for 15 min. All remaining steps were carried out as detailed under film preparation/hydration section above.

Preparation of Films Containing 5000 ppm Brimonidine Tartrate

Initial stages as per the Procedure in the preparation of control insert film_brimonidine. Following the addition of PEG and 30 min of stirring, 10 ml of a 1.06 mg/ml brimonidine tartrate solution in DI water was added and the mixture was stirred for 15 min. All remaining steps were carried out as detailed under film preparation/hydration section above.

Measurement of Various Film Properties for Brimonidine Tartrate Films and Current Formulation Films A series of physical properties were measured for Brimonidine Tartrate doped films. The procedures for each property measurement are outlined below and the results summarized in TABLE 1.

Dissolution Time:

6 mm diameter film disks were cut and placed in a separate 4 ml vials. DI water (2 ml) was added to each vial and capped. Each vial was vigorously shaken by hand until the insert had dissolved by visual inspection. The dissolution time was recorded.

Formulation Ph:

After obtaining a homogeneous formulation solution, the pH of the solution is measured using an OakIon pH meter.

Mechanical Tests:

1-1.5×4 cm film strips were cut and then hydrated for 36-48 hours in separate sealed aluminum foil bags containing 60 μL DI water. The resultant hydrated film strips were then subjected to mechanical tests [Young's modulus and % Elongation at break] using an Instron testing machine. Presented below in TABLE 1 below, is a summary of the physical characterization of the insert film characteristics.

| Test Parameter | Control Insert with about 100 ppm Brimonidine Tartrate | Control Insert with about 500 ppm Brimonidine Tartrate | Control Insert with about 5000 ppm Brimonidine Tartrate | Control Insert Formulation_Brimonidine Tartrate |
|---|---|---|---|---|
| Dissolution Time (min) | 5.21 | 4.88 | 4.6 | 3.42 |
| pH | 7.4 | 7.4 | 7.1 | 7.28 |
| Elongation (%) | 76.13(wet) | 92.15(wet) | 86.82(wet) | 85.55(wet) |
| Modulus (MPa) | 0.38(wet) | 0.38(wet) | 0.27(wet) | 0.30(wet) |

The mechanical stability of the brimonidine containing insert films were tested at time zero and at 25° C. and 37° C. and are shown in TABLE 2 below. The brimonidine containing insert films showed excellent mechanical stability at 45 days under 25° C. and 37° C. The wet thickness increased modestly over time relative to time zero.

| | Time = 0 Days | | T = 45 Days (25° C.) | | T = 45 Days (37° C.) | |
|---|---|---|---|---|---|---|
| | ~500 ppm | ~5000 ppm | ~500 ppm | ~5000 ppm | ~500 ppm | ~5000 ppm |
| Wet Thickness (mm) | 0.115 | 0.11 | 0.13 | 0.121 | 0.137 | 0.131 |
| Tensile Strength (MPa) | 0.111 | 0.099 | 0.038 | 0.053 | 0.043 | 0.036 |
| Modulus (MPa) | 0.164 | 0.26 | 0.247 | 0.27 | 0.269 | 0.272 |

Example 2—Polymeric Eye Insert Containing PLGA

Addition of PLGA (MW:10,000 to 18,000 and 96,000) to the polymeric insert composition at different concentrations (1%, 1.7%, 2% and 4%) were evaluated. PLGA doped films demonstrated similar profile to undoped films. Presence of PLGA slowed the dissolution rate with no significant changes to the mechanical properties of the film. There was a clear effect of PLGA concentration and molecular weight on dissolution profile.

PLGA Solubility Screening:

Both low or high MW PLGA were found to be insoluble in DI water, ethanol, amyl-alcohol, Methanol and PEG 400. Both low and high MW PLGA were found to be soluble in DCM, THF, EA and acetone. Both low and high MW PLGA will be introduced into the current formulation as a solution in acetone.

Preparation of control Insert Film_PLGA:

300 mL of DI water was transferred from a graduated cylinder to a clean 500 mL Erlenmeyer flask. HA (0.84 g) and PVP (0.21 g) were added into the 500 mL Erlenmeyer flask. After stirring the mixture for 1.5 hrs, a homogenous solution was obtained. HP Guar (0.84 g) was added and the mixture was stirred for one hour, after which the mixture was once again homogenous. PEG (0.21 g) was added and the mixture was stirred for an additional 30 minutes. The mixture was then allowed to stand (no stirring) for 30 min to remove air bubbles. The mixture (150 g) was poured into a petri dish which was then placed into an evaporation oven (27±3° C.) for two days to produce a film.

Insert Film Hydration Procedure: The film was cut into 6 mm disks with a disk cutter. Note: Each disk was measured for thickness before hydration. Two disks were placed into the middle of a pouch which contained 3 μl of DI water at one bottom corner of the pouch. The pouch was sealed with a heat sealer.

Preparation of Films Containing 1.7% Low MW PLGA:

Initial stages as per the procedure in Preparation of control Insert Film_PLGA. Following the addition of PEG and 30 min of stirring, 2.2 ml of an 81.4 mg/5 ml low MW PLGA solution in acetone was added and the mixture was stirred for 30 min. All remaining steps were carried out as detailed in the insert preparation section.

Preparation of Films Containing 0.94% High MW PLGA:

Initial stages as per the procedure in Preparation of control Insert Film_PLGA. Following the addition of PEG and 30 min of stirring, 1.1 ml of a 90 mg/5 ml high MW PLGA solution in acetone was added and the mixture was stirred for 30 min. All remaining steps were carried out as detailed in the insert preparation section.

Preparation of Films Containing 1.94% Low MW PLGA:

Initial stages as per the procedure in Preparation of control Insert Film_PLGA. Following the addition of PEG and 30 min of stirring, 10 ml of a 4.08 mg/ml low MW PLGA solution in acetone was added and the mixture stirred for 1.5 hrs. The solution was slightly hazy. All remaining steps were carried out as detailed in insert preparation section.

Preparation of Films Containing 2.02% High MW PLGA:

Initial stages as per the procedure in Preparation of control Insert Film_PLGA. Following the addition of PEG and 30 min of stirring, 10 ml of a 4.25 mg/ml high MW PLGA solution in acetone was added and the mixture was stirred for 1.5 hrs. The solution was hazy. All remaining steps were carried out as detailed in the insert preparation section.

Preparation of Films Containing 4.07% Low MW PLGA:

Initial stages as per the procedure in Preparation of control Insert Film_PLGA. Following the addition of PEG and 30 min of stirring, 10 ml of an 8.55 mg/ml high MW PLGA solution in acetone was added and the mixture stirred for 1.5 hrs. The solution was hazy. All remaining steps were carried out as detailed in insert preparation section.

Measurement of Various Film Properties for PLGA Film and Current Formulation Films A series of physical properties (funnel test) were measured for both PLGA doped films and current formulation films. The procedures for each property measurement are outlined below and the results are summarized in the table below.

Dissolution Time:

6 mm diameter film disks were cut and placed in separate 4 ml vials. DI water (2 ml) was added to each vial and capped. Each vial was vigorously shaken by hand until the insert had dissolved by visual inspection. The dissolution time was recorded.

Formulation pH:

After obtaining a homogeneous formulation solution, the pH of the solution is measured using an OaklIon pH meter.

Mechanical Tests:

1-1.5×4 cm film strips were cut and then hydrated for 36-48 hours in separate sealed aluminum foil bags containing 30 μL added DI water. The resultant hydrated film strips were then subjected to mechanical tests [Young's modulus and % Elongation at break] using an Instron testing machine.

Summarized below are the test parameter results for the different PLGA doped films

| Test Parameter | Control insert plus 1.7% Low MW PLGA Film | Control insert plus 1% High MW PLGA Film | Control Insert Formulation_PLGA |
|---|---|---|---|
| Dissolution Time (min) | 3.3 | 5.33 | 2 |
| pH | 7.54 | 6.95 | 7.28 |
| Elongation (%) | 149.71 (wet) | 176.22 (wet) | 85.55 (wet) |
| Modulus (MPa) | 0.22 (wet) | 0.162 (wet) | 0.298 (wet) |

| Test Parameter | Control insert plus 2% High MW PLGA Film | Control insert plus 2% Low MW PLGA Film | Current Insert Formulation |
|---|---|---|---|
| Dissolution Time (min) | 4.18 | 3.1 | 2 |
| pH | 6.83 | 6.79 | 7.28 |
| Elongation (%) | 99.24 (wet) | 115.21 (wet) | 91.33 (wet) |
| Modulus (MPa) | 0.29 (wet) | 0.26 (wet) | 0.32 (wet) |

| Test Parameter | Control insert plus 4% Low MW PLGA Film | Control insert plus 4% High MW PLGA Film | Control Insert Formulation_PLGA |
|---|---|---|---|
| Dissolution Time (min) | 5 | 3.83 | 2 |
| pH | 6.56 | 6.55 | 7.28 |
| Elongation (%) | 62.11 (wet) | 66.84 (wet) | 87.14 (wet) |
| Modulus (MPa) | 0.273 (wet) | 0.476 (wet) | 0.405 (wet) |

Example 11—Polymeric Eye Insert Containing a TRPM8 Agonist (Menthone Glycerin Acetal)

Addition of MGA to the polymeric insert composition at 20 ppm and 40 ppm were evaluated. MGA doped films demonstrated similar color and transparency to undoped films. Presence of MGA altered the folded endurance results significantly. The MGA doped dry films suffered cracking/breaking after less than 20 folding cycles. On the contrary, hydrated films doped and undoped demonstrated similar folding endurance characteristic.

Preparation of Control Insert Films_MGA:

800 ml of DI water was transferred from a graduated cylinder to a clean 1000 ml Erlenmeyer flask. HA (2.24 g) and PVP (0.56 g) were added into the 1000 ml Erlenmeyer flask. The mixture was stirred via mechanical stirring and simultaneously sonicated. After a total of 1.5 hrs, the mixture was observed to be homogenous. HP Guar (2.24 g) was added and the mixture was stirred with sonication again. After one hour, the mixture was once again homogenous. PEG (0.56 g) was added and the mixture was stirred and sonicated for an additional 30 min. Stirring was then stopped. The mixture was allowed to continue sonicating for 30 min more in order to remove air bubbles. After sonication, the mixture was allowed to rest on the bench for 30 min. The mixture (150 g) was poured into a petri dish. The film formed after evaporation in a 27+−3° C. oven for two days.

Insert Film Hydration Procedure: The film was cut into 6 mm disks with a disk cutter. Note: Each disk was measured for thickness before hydration. Two disks were placed into the middle of a pouch which contained 3 μl of DI water at one bottom corner of the pouch. The pouch was sealed with a sealer.

Preparation of Films Containing 20 ppm MGA:

Initial stages as per the film preparation procedure above. Following the addition of PEG and 30 min stirring/sonication, 140 µl of a 0.84 mg/ml MGA solution in DI water-MeOH (2/1) was added and the mixture stirred with sonication for 15 min. All remaining steps were carried out as detailed in film preparation procedure.

Preparation of Films Containing 40 ppm MGA:

Initial stages as per the film preparation procedure above. Following the addition of PEG and 30 min stirring/sonication, 280 µl of a 0.84 mg/ml MGA solution in DI water-MeOH (2/1) was added and the mixture stirred with sonication for 15 min. All remaining steps were carried out as detailed in the film preparation procedure. Summarized below are the physical test results of the MGA doped films.

Measurement of Various Film Properties for MGA-Doped and Current Formulation Films Various film properties (funnel tests) were measured for both MGA-doped and current formulation films. The procedures for each property measurement are outlined below and the results summarized in table below.

Dissolution Time:

6 mm diameter film disks were cut and placed in a separate 4 ml vials. DI water (2 ml) was added to each vial and capped. Each vial was vigorously shaken by hand until the insert had dissolved by visual inspection. The dissolution time was recorded.

Formulation pH:

After obtaining a homogeneous formulation solution, the pH of the solution was measured using a OakIon pH meter.

Mechanical Tests:

1×4 cm film strips were cut and then hydrated for 24 hours in separate sealed aluminum foil bags containing 60 µL added DI water. The resultant hydrated film strips were then subjected to mechanical tests [Young's modulus and % Elongation at break] using an Instron.

| Test Parameter | Control Insert plus 20 ppm MGA Film | Control Insert plus 40 ppm MGA Film | Control Insert Formulation_MGA |
|---|---|---|---|
| Dissolution Time (min) | 3.33 | 3.22 | 4.62 |
| pH | 7.55 | 7.42 | 7.75 |
| Elongation (%) | 69.96 (wet) | 49.72 (wet) | 54.47 (wet) |
| Modulus (MPa) | 0.567 | 0.522 | 0.437 |

The invention claimed is:

1. A polymeric eye insert, the insert comprising: a biodegradable polymer and one or more mucoadhesive polymers that are biocompatible with the ocular surface and tear film of the eye, wherein the biodegradable polymer is present in an amount of from 0.5% to 10% w/w; wherein the biodegradable polymer increases a dissolution time of the polymeric eye insert by at least 15 percent comparing to the control polymeric eye insert which is the same polymeric eye insert except the biodegradable polymer is not present.

2. The polymeric eye insert of claim 1, wherein the biodegradable polymer is poly(lactic-co-glycolic) acid (PLGA), or polylactic acid (PLA).

3. The polymeric eye insert of claim 2, wherein the biodegradable polymer is poly(lactic-co-glycolic) acid (PLGA).

4. The polymeric eye insert of claim 1, wherein the one or more mucoadhesive polymers are selected from the group consisting of: hyaluronic acid or salts thereof, hydroxypropylmethylcellulose (HPMC), methylcellulose, tamarind seed polysaccharide (TSP), guar, hydroxypropyl guar (HP guar), scleroglucan poloxamer, poly(galacturonic) acid, sodium alginate, pectin, xanthan gum, xyloglucan gum, chitosan, sodium carboxymethylcellulose, polyvinyl alcohol, polyvinyl pyrrolidine, carbomer, polyacrylic acid and combinations thereof.

5. The polymeric eye insert of claim 4, wherein the one or more mucoadhesive polymers are HP guar, hyaluronic acid, sodium hyaluronate or polyvinyl pyrrolidine.

6. The polymeric eye insert of claim 1, wherein the one or more mucoadhesive polymers are present in an amount of from about 50% to about 90% w/w, about 60% to about 85% w/w, about 70% to about 85% w/w, or about 80% to about 90% w/w of the polymeric eye insert, provided that the sum of the % w/w of mucoadhesive polymers and % w/w of the biodegradable polymer and other components not listed above is 100% w/w.

7. The polymeric eye insert of claim 1, further comprising a plasticizer or softener.

8. The polymeric eye insert of claim 7, wherein the plasticizer or softener is selected from the group consisting of: polyethylene glycol (PEG), a PEG derivative, water, Vitamin E, and triethyl citrate.

9. The polymeric eye insert of claim 7, wherein the plasticizer or softener is present in an amount of from about 2% to about 25% w/w, about 5% to about 20% w/w, about 5% to about 15% w/w, or about 5% to about 10% w/w of the polymeric eye insert, provided that the sum of the % w/w of mucoadhesive polymers and % w/w of the biodegradable polymer, % w/w of the plasticizer or softener and other components not listed above is 100% w/w.

10. The polymeric eye insert of claim 8, wherein the plasticizer or softener is PEG.

11. The polymeric eye insert of claim 10, wherein the control insert is comprised of approximately 38.5% w/w HP guar, approximately 9.5% w/w PVP, approximately 38.5% w/w sodium hyaluronate, 5% w/w PLGA, and approximately 9.5% PEG.

12. The polymeric eye insert of claim 1, further comprising 1-5000 ppm alpha-2 adrenergic receptor agonist.

13. The polymer eye insert of claim 1, further comprising 10-100 ppm Menthone Glycerin Acetal.

14. The polymeric eye insert of claim 1, wherein the insert shape is a film, a rod, a sphere, an annulus, or an irregular shape having a maximum size in any single dimension of 5-6 mm.

15. The polymeric eye insert of claim 1, wherein said insert has a circular shape about 5 mm in diameter, a thickness of 50-400 µm, and a water content of 1% to 50% w/w.

16. The polymeric eye insert of claim 1, wherein said insert has a thickness of about 150-250 µm, and a water content of 30 to 50% w/w.

17. The polymeric eye insert of claim 5, wherein said HP guar has a weight average molecular weight of 2 to 4 million Daltons and said sodium hyaluronate has a weight average molecular weight of 0.1 to 2 million Daltons.

18. A method of treating an ocular disorder, which comprises applying the polymeric eye insert of claim 1 to the cul-de-sac of the eye.

19. A method according to claim 18, wherein said ocular disorder is selected from the group consisting of dry eye, eye redness, myopia, glaucoma, allergy, infection and inflammation.

* * * * *